US012728012B2

(12) United States Patent
Leemrijse et al.

(10) Patent No.: US 12,728,012 B2
(45) Date of Patent: Sep. 8, 2026

(54) IMPLANTABLE COMPONENT WITH IMPROVED ANCHORING MEANS FOR ANKLE PROSTHESIS AND ANKLE PROSTHESIS COMPRISING SUCH A COMPONENT

(71) Applicant: IN2BONES, Ecully (FR)

(72) Inventors: Thibaut Jean Pierre Henry Leemrijse, Brussels (BE); Pit Putzeys, Bridel (LU); Laurent François René Paul, Mellery (BE); Per-Henrik Agren, Stockholm (SE); Jean-Luc Pierre Marie Besse, Chaponnay (FR)

(73) Assignee: IN2BONES, Ecully (FR)

( * ) Notice: Subject to any disclaimer, the term of this patent is extended or adjusted under 35 U.S.C. 154(b) by 266 days.

(21) Appl. No.: 17/156,078

(22) Filed: Jan. 22, 2021

(65) Prior Publication Data

US 2021/0220143 A1 Jul. 22, 2021

(30) Foreign Application Priority Data

Jan. 22, 2020 (FR) ...................................... 2000621

(51) Int. Cl.
*A61F 2/42* (2006.01)
*A61F 2/30* (2006.01)

(52) U.S. Cl.
CPC .. *A61F 2/4202* (2013.01); *A61F 2002/30179* (2013.01); *A61F 2002/30884* (2013.01); *A61F 2002/30896* (2013.01); *A61F 2002/4205* (2013.01); *A61F 2002/4207* (2013.01); *A61F 2002/4212* (2013.01)

(58) Field of Classification Search
CPC ...... A61F 2002/4205; A61F 2002/4207; A61F 2002/30896
See application file for complete search history.

(56) References Cited

U.S. PATENT DOCUMENTS

| | | | | |
|---|---|---|---|---|
| 11,432,932 | B2 * | 9/2022 | Hwa | A61F 2/3859 |
| 2003/0060884 | A1 * | 3/2003 | Fell | A61F 2/38 623/14.12 |
| 2003/0204265 | A1 | 10/2003 | Short et al. | |

(Continued)

FOREIGN PATENT DOCUMENTS

| | | |
|---|---|---|
| WO | 2019/045412 A1 | 3/2019 |
| WO | 2019/220048 A1 | 11/2019 |

*Primary Examiner* — Megan Y Wolf

(74) *Attorney, Agent, or Firm* — Rutan & Tucker LLP; Hani Z. Sayed

(57) ABSTRACT

An implantable ankle-prosthesis component (1), comprising a main body (2) with a bone contact face (3) intended to come into contact with an area of a bone body of an ankle and extending along a median contact plane (Pc), and comprising a anchoring means (4) protruding from the bone contact face (3), the anchoring means (4) comprising two pairs (20A, 20B) of anchoring wings, each extending in a plane (P1, P2), respectively, orthogonal to said median contact plane (Pc) between a first end (23A, 23B) connected to said bone contact face (3) and an opposite second end (24A, 24B), the planes of extension (P1, P2) of the pairs (20A, 20B) of anchoring wings intersecting each other, said second ends (24A, 24B) of the pairs (20A, 20B) of anchoring wings being inscribed in a leading plane (Pa) inclined with respect to said median contact plane (Pc).

13 Claims, 8 Drawing Sheets

(56) References Cited

U.S. PATENT DOCUMENTS

| | | | | |
|---|---|---|---|---|
| 2004/0167631 | A1* | 8/2004 | Luchesi | A61F 2/4202 623/21.18 |
| 2010/0249941 | A1* | 9/2010 | Fell | A61F 2/3836 623/20.28 |
| 2011/0035019 | A1 | 2/2011 | Goswami et al. | |
| 2020/0188126 | A1* | 6/2020 | Lee | A61F 2/42 |
| 2020/0330238 | A1* | 10/2020 | Calamel | A61F 2/4202 |

* cited by examiner

[Fig 1]
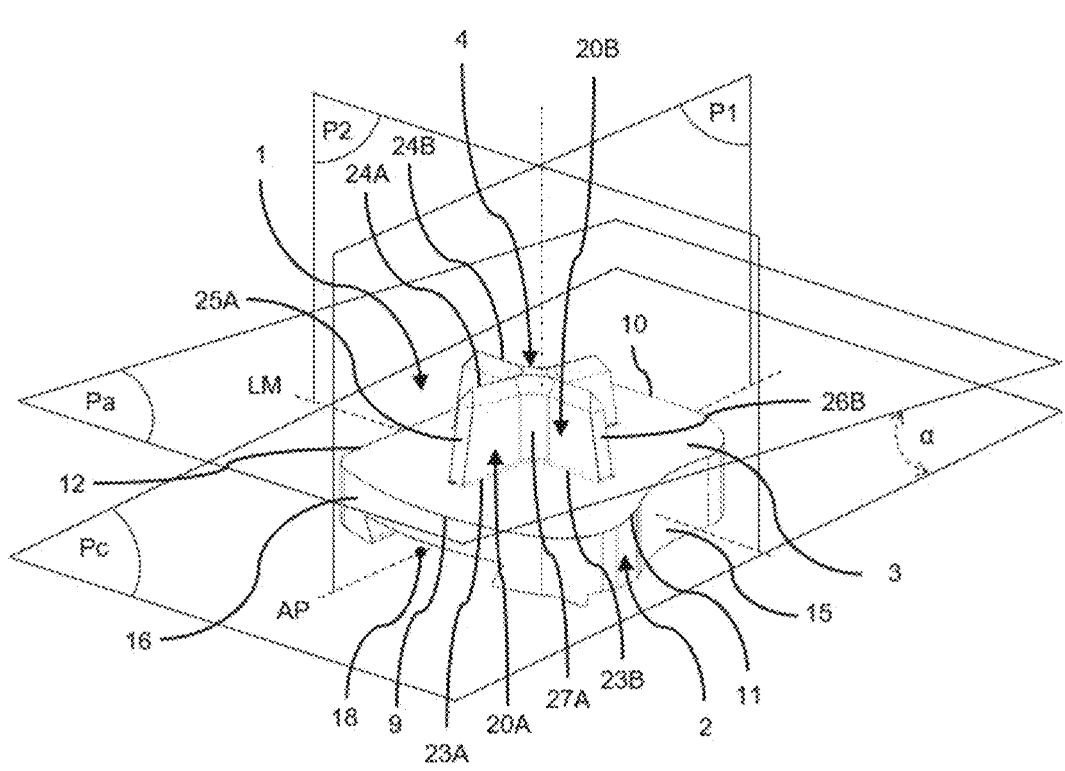

[Fig 2]
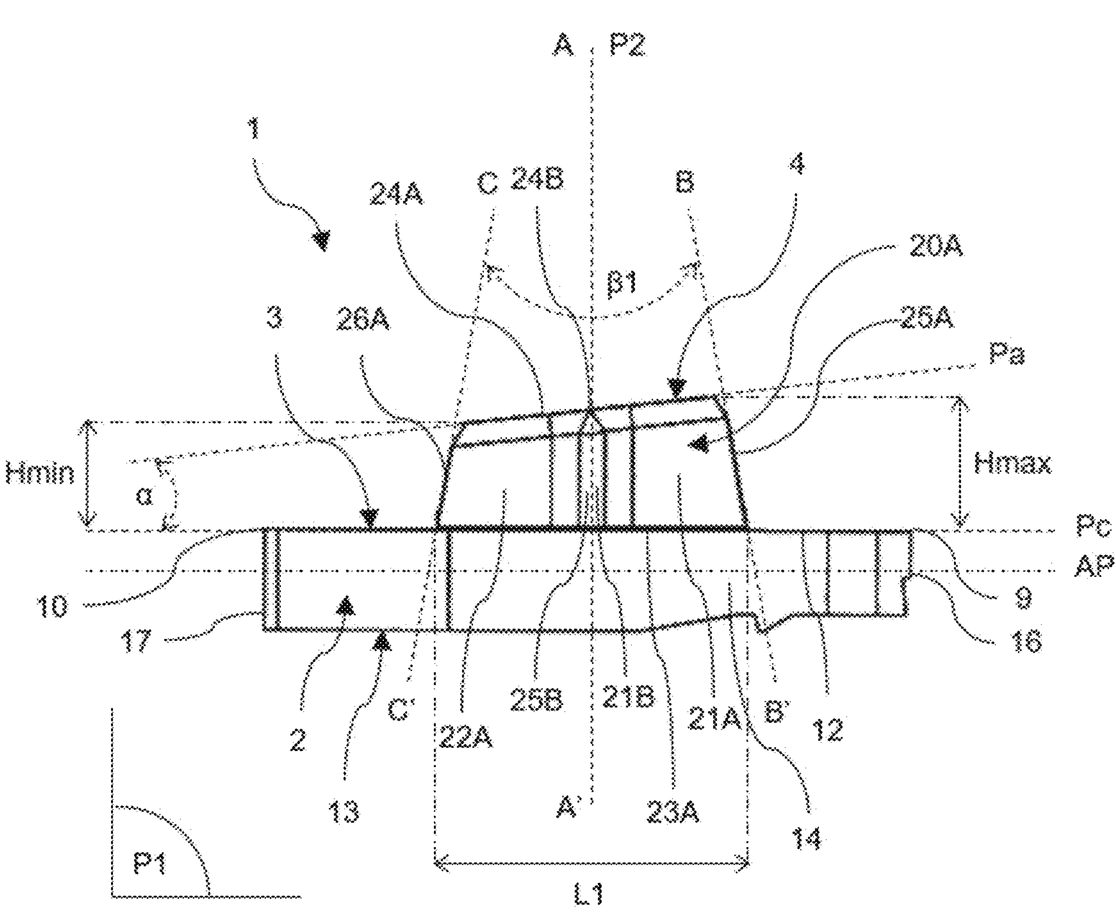

[Fig 3]
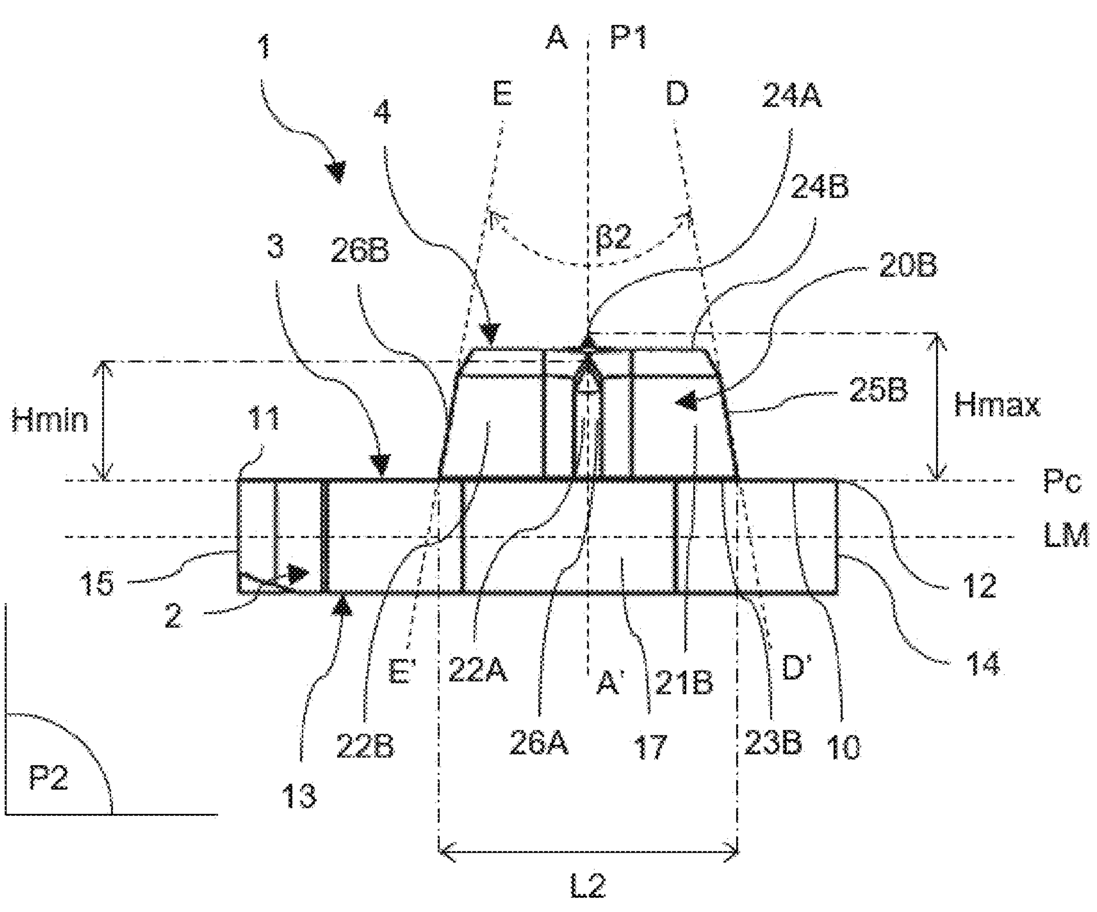

[Fig 4]
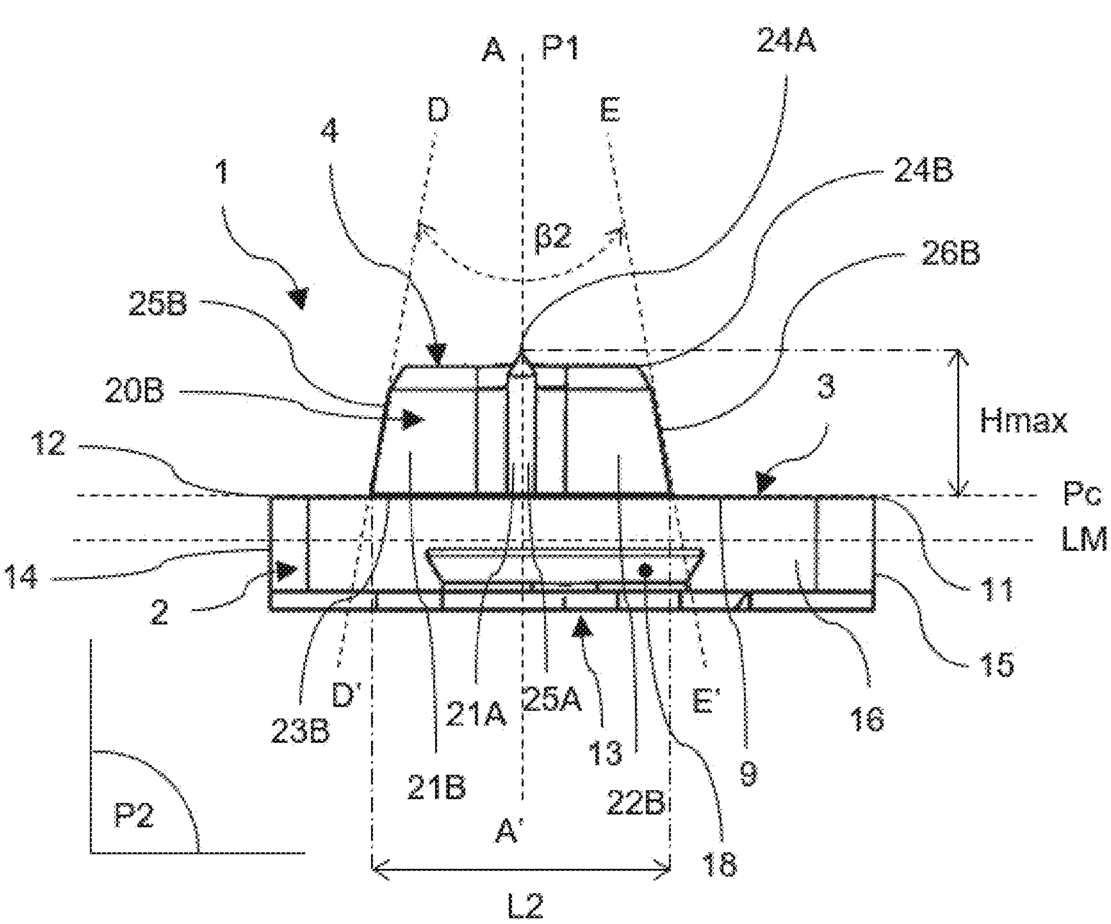

[Fig 5]
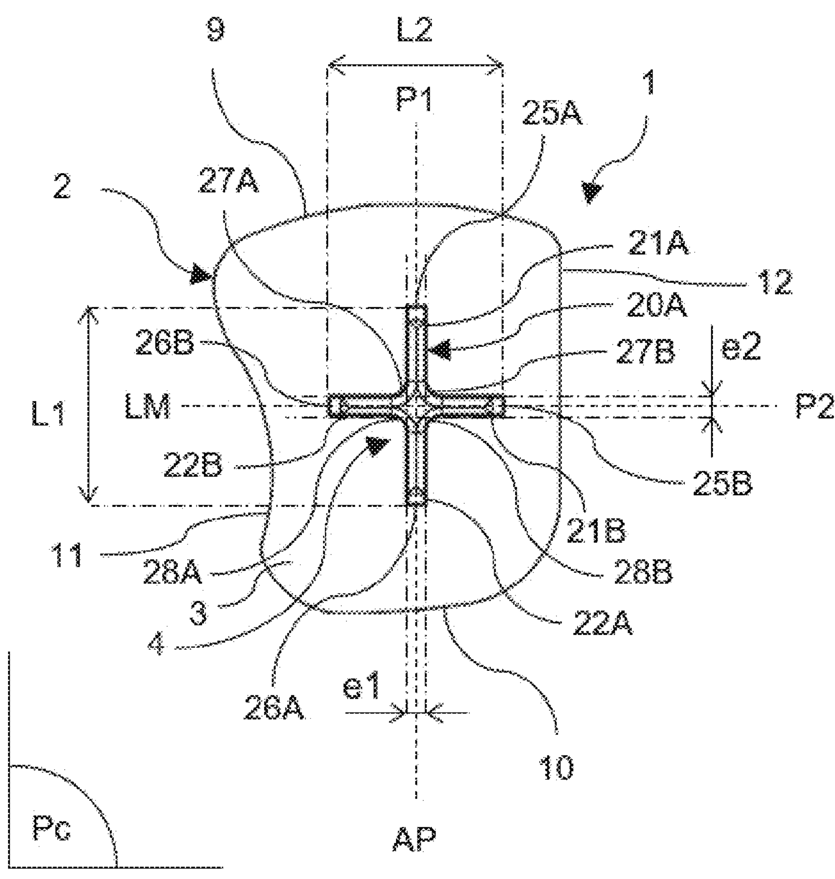

[Fig 6]
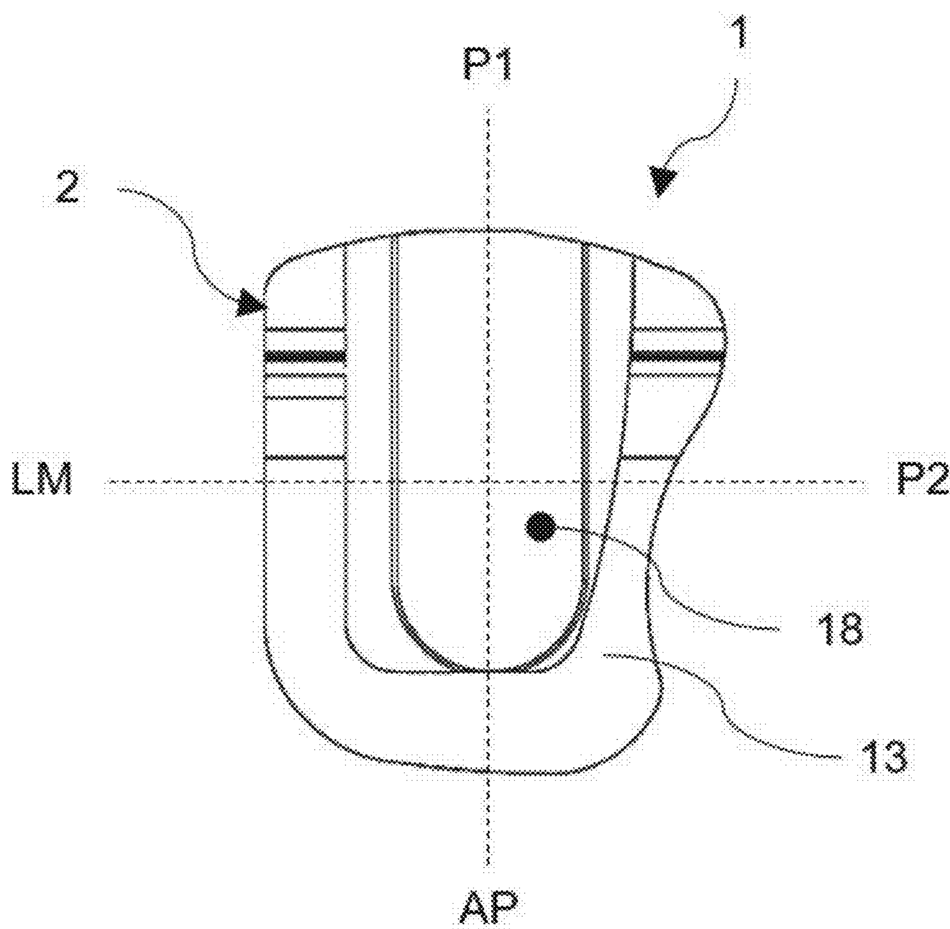

[Fig 7]
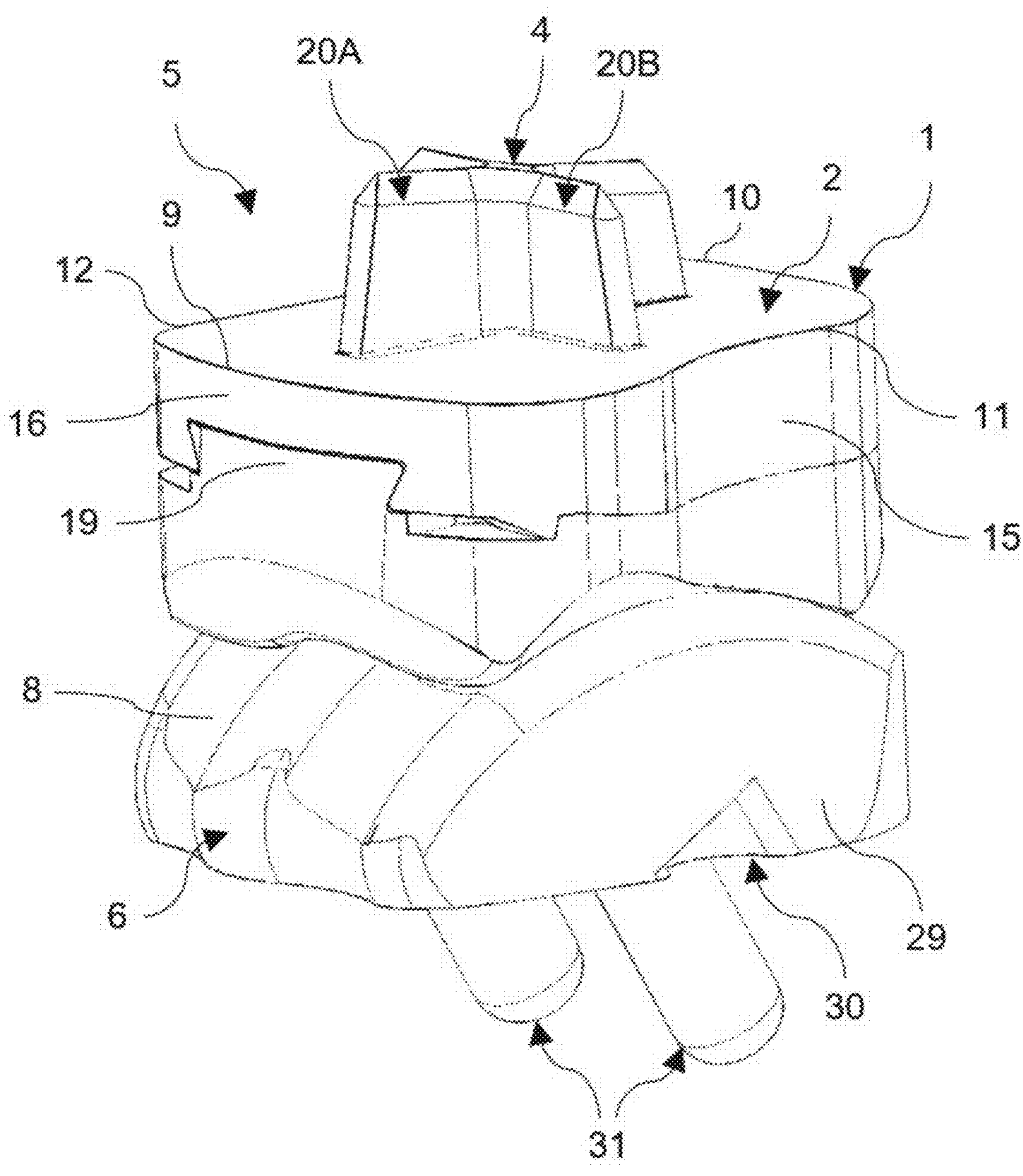

[Fig 8]
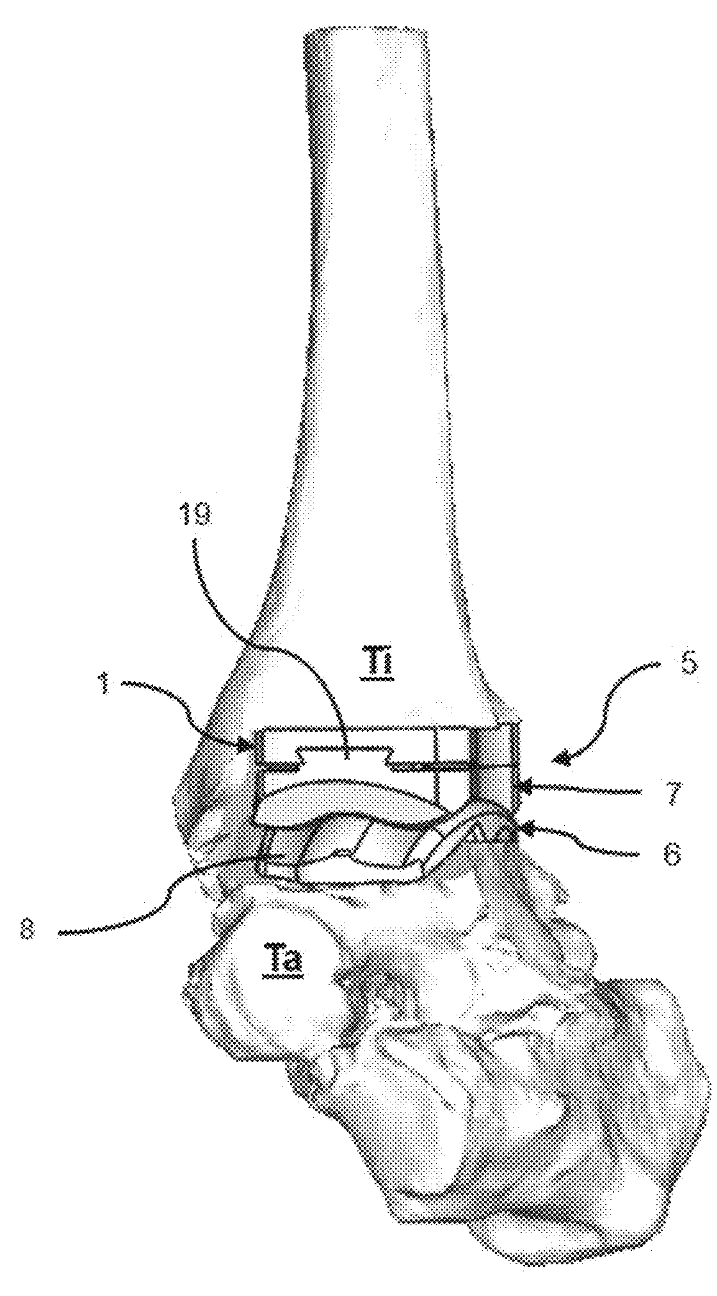

IMPLANTABLE COMPONENT WITH IMPROVED ANCHORING MEANS FOR ANKLE PROSTHESIS AND ANKLE PROSTHESIS COMPRISING SUCH A COMPONENT

The invention relates to the general field of ankle prostheses, i.e. implantable devices for ankle joint replacement, in particular within the framework of an orthopaedic treatment.

The invention more particularly relates to an implantable ankle-prosthesis component, said component comprising a main body provided with a bone contact face that is intended to be arranged in contact with an area of a bone body of an ankle and that extends along a median contact plane, said component comprising at least one anchoring means that protrudes from said bone contact face to anchor said component into said bone body.

The invention also relates to an ankle prosthesis comprising at least one implantable component.

To treat certain bone pathologies of the ankle, such as arthrosis, causing a degradation or a disappearance of the joint cartilage, it is known to proceed to an arthrodesis of the tibiotarsal joint. Such an arthrodesis operation aims to limit, or even totally block, the ankle mobility by osteosynthesis, in order to stop the joint pain felt by the patient. Although arthrodesis of the tibiotarsal joint gives generally satisfaction, its main drawback lies precisely in the suppression of the joint mobility, which has hence to be compensated as much as possible by the other joints of the patient's leg. A long period of adaptation is then necessary for the patient to recover, after the operation, satisfying locomotive abilities. Moreover, blocking the tibiotarsal joint generates high mechanical stresses on the neighbour joints, which are then exposed to a high risk of premature degeneration.

That is the reason why it has be proposed to proceed, in certain situations, to ankle arthroplasty as an alternative to arthrodesis, that is to say the total or partial replacement of the damaged ankle joint by an artificial, prosthetic joint.

Various ankle prostheses have hence been introduced, which are formed of one or several implantable components, in order to replace all or part of a damage ankle joint. In particular, an ankle prosthesis is known, which is formed of a plurality of implantable components, that is to say a talar component and a tibial component, intended to be anchored to the talus and the tibia, respectively, and a plastic pad that is designed to be interposed between the talar component and the tibial component and to be articulated in contact with the talar component.

The use of such known prostheses makes it possible, contrary to the conventional arthrodesis, to keep a good mobility of the patient's ankle, hence facilitating the walk, and to preserve the different joints of the patient's foot and leg. However, it has been observed that the known ankle prostheses are still perfectible, in particular as regards the mechanical strength of the bone anchoring of the component (s) thereof, but also as regards the convenience and accuracy of positioning of the implantable component(s) into the patient's body.

Consequently, the objects assigned to the present invention aim to propose a new implantable ankle-prosthesis component, as well as a new ankle prosthesis comprising such a component, the latter comprising a means for anchoring the component into a bone body of an ankle permitting both a particularly reliable bone anchoring of the component and a particularly easy and accurate positioning of said component into the patient's body.

Another object of the invention aims to propose a new implantable component and a new ankle prosthesis whose positioning is both rapid and particularly low-traumatic for the patient.

Another object of the invention aims to propose a new implantable component and a new ankle prosthesis, which are particularly robust and strong.

Another object of the invention aims to propose a new implantable component and a new ankle prosthesis of simple design and whose manufacturing is particularly easy.

Another object of the invention aims to propose a new implantable component and a new ankle prosthesis making it possible to reduce the cost of the surgical operation of an ankle.

Another object of the invention aims to propose a new implantable component and a new ankle prosthesis making it possible to reduce the risk for the patient's health.

Another object of the invention aims to propose a new implantable component and a new ankle prosthesis making it possible to treat a bone pathology of the patient in particularly efficient and rapid manner.

The objects assigned to the invention are achieved by means of an implantable ankle-prosthesis component, said component comprising a main body provided with a bone contact face that is intended to be arranged in contact with an area of a bone body of an ankle and that extends along a median contact plane, said component comprising at least one anchoring means that protrudes from said bone contact face to anchor said component into said bone body, said component being characterized in that said anchoring means comprises two pairs of anchoring wings, which each respectively extend in a plane orthogonal to said median contact plane of the bone contact face between a first end connected to said bone contact face and an opposite second end, said respective planes of extension of the pairs of anchoring wings intersecting each other, said second ends of the pairs of anchoring wings being inscribed in a leading plane inclined with respect to said median contact plane.

The objects assigned to the invention are also achieved by means of an ankle prosthesis comprising at least one implantable component, characterized in that said implantable component is in accordance with the above.

Other features and advantages of the invention will appear in more detail upon reading of the following description, with reference to the appended drawings, given by way of purely illustrative and non-limitative examples, in which:

FIG. 1 illustrates, in a perspective view, a preferential embodiment of an implantable component in accordance with the invention, which advantageously constitutes a tibial ankle-prosthesis component;

FIG. 2 illustrates, in a medial view, the implantable component of FIG. 1;

FIG. 3 illustrates, in a posterior view, the implantable component of FIGS. 1 and 2;

FIG. 4 illustrates, in an anterior view, the implantable component of FIGS. 1 to 3;

FIG. 5 illustrates, in a top view, the implantable component of FIGS. 1 to 4;

FIG. 6 illustrates, in a bottom view, the implantable component of FIGS. 1 to 5;

FIG. 7 illustrates, in a perspective view, an embodiment of an ankle prosthesis in accordance with the invention, which prosthesis comprises the implantable component of FIGS. 1 to 6;

FIG. 8 illustrates, in a perspective view, the ankle prosthesis of FIG. 7, implanted at a patient's left foot in replacement of the anatomical tibiotarsal joint.

According to a first aspect, the invention relates, on the one hand, to an implantable ankle-prosthesis component 1, intended to be added to a bone body Ti, Ta of an ankle to be treated. The implantable component 1 in accordance with the invention comprises for that purpose a main body 2 provided with a bone contact face 3, which is intended to be arranged in contact with an area of a bone body Ti, Ta of an ankle, as well as at least one anchoring means 4 that protrudes from said bone contact face 3 to anchor said component 1 into said bone body Ti, Ta. According to a second aspect, the invention relates to an ankle prosthesis 5 comprising at least such an implantable component 1.

The ankle prosthesis 5 comprising an implantable component 1 in accordance with the invention constitutes a medical device, surgically implantable into the body of a patient, which is intended to replace all or part of a tibiotarsal joint of said patient. For that purpose, such a prosthesis 5 and the implantable component 1 thereof are designed to be inserted and interposed between a distal end of a tibia Ti and a corresponding talus Ta (or astragal) of the patient's ankle. Advantageously, the considered tibia Ti and/or talus Ta will have been given, previously to the positioning of the prosthesis 5 in the patient's body, a suitable preparation, and for example an extraction of cartilage elements and bone cuts, so as to eliminate all or part of the natural joint surfaces of the tibiotarsal joint to be treated.

Advantageously, the implantable component 1 of the invention more specifically constitutes a tibial component 1 of an ankle prosthesis 5, whose bone contact face 3 is hence for that purpose specifically intended to be arranged in contact with an area of a distal end of a tibia Ti. A preferential embodiment of an implantable component 1, in accordance with the invention, constituting such a tibial component 1 of an ankle prosthesis 5 is illustrated by way of example in FIGS. 1 to 6. Reciprocally, the ankle 10 prosthesis 5 of the invention advantageously comprises such an implantable component 1 constituting a tibial component 1 and whose bone contact face 3 is intended to be arranged in contact with an area of a distal end of a tibial Ti. An embodiment of such an ankle prosthesis 5 is illustrated by way of example in FIG. 7. The implantable component 1 and the prosthesis 5 illustrated by way of example in the figures are intended to be positioned at a patient's left foot, as illustrated in situation in FIG. 8. Of course, the invention also covers a component 1 and a prosthesis 5 that would be intended to be positioned at the patient's right feet. Advantageously, these latter would then be defined by symmetry, with respect to the patient's sagittal plane, of the component 1 and prosthesis 5 illustrated in the figures.

Advantageously, as in the embodiment illustrated in the figures, said prosthesis 5 is designed to replace totally the concerned tibiotarsal joint (total ankle prosthesis, TAP). For that purpose, the prosthesis 5 comprises at least one implantable component 1, which is in accordance with the invention and which constitutes a tibial component 1, and a talar component 6, which is also intended to be implanted into the body of a patient an ankle joint of whom is to be treated. Whereas the tibial component 1 is intended to be arranged, added, in contact with an area of a distal end of a tibia Ti, in accordance with what precedes, the talar component 6 is intended to be arranged, added, in contact with an area of a corresponding talus Ta (or astragal) of a patient's ankle. Said tibial component 1 and talar component 6 are then designed to cooperate, directly or indirectly, with each other so as to form a prosthetic joint capable of reproducing with the highest fidelity the natural kinematics of the anatomical ankle.

Even so, the implantable component in accordance with the invention could possibly constitute a talar component of an ankle prosthesis. It could moreover constitute a component of a prosthesis designed to replace only a part of a tibiotarsal joint to be treated. Thus, said implantable component according to the invention could constitute a tibial component designed to cooperate, directly or indirectly, with an anatomical joint surface of a talus Ta, in the hypothesis in which only the distal end of the tibia Ti is damaged and requires to be treated and equipped with a prosthetic joint surface. As an alternative, said implantable component could constitute a talar ankle-prosthesis component designed to cooperate, directly or indirectly, with an anatomical joint surface of a tibia Ti, in the hypothesis is which only the joint surface of the talus Ta is damaged and requires to be treated and equipped with a prosthetic joint surface.

Reciprocally, the ankle prosthesis 5 of the invention could comprise an implantable component 1 in accordance with the invention, unique or not, which would constitute a talar component of said prosthesis 5, or also comprise a tibial component and a talar component, both in accordance with the invention.

In the case where the prosthesis 5 is designed to totally replace a tibiotarsal joint, said ankle prosthesis 5 can further advantageously comprise, in addition to said tibial 1 and talar 6 components, an intermediate component 7 (or pad, or also insert), which is designed to be interposed between said talar component 6 and said tibial component 1, as illustrated by way of examples in FIGS. 7 to 10. Said intermediate component 7 advantageously comprises an intermediate joint surface designed to cooperate with a corresponding talar joint surface 8 of the talar component 6. Said intermediate component 7 comprises a tibial interface surface with the tibial component 1, to said intermediate joint surface. In the embodiments of component 1 and prosthesis 5 illustrated in the figures, such an intermediate component 7 is designed to be fastened to the tibial component 1, and immobilized with respect to the latter, by means of said tibial interface surface, so as to form a so-called "two-component" ankle prosthesis. However, according to a variant that is not illustrated, the tibial component and the intermediate component could, as an alternative, be designed so as to allow a mobility of the intermediate component with respect to the tibial component, by cooperation of the tibial interface surface of the intermediate component with a corresponding surface of the tibial component. The ankle prosthesis would then form a so-called "three-component" prosthesis. It should be noted that, to form a so-called "two-component" ankle prosthesis 5, it is also possible to provide that the above-mentioned tibial 1 and intermediate 7 components are not distinct from each other, but form on the contrary a single and same component, potentially monolithic. Nevertheless, the intermediate component 7 constituting a wearing part, due to its interaction with the talar joint surface 8 of the talar component 6, it is advantageous that the intermediate component 7 can be distinct from the tibial component 1, and removably fastened to the latter so as to permit the later replacement thereof if necessary. In the case where the intermediate component 7 is distinct from the tibial component 1, and fastened or not to the latter, said intermediate component 7 is preferentially, as such, a one-piece part made of material having a low friction coefficient, for example a plastic material such as high-density polyethylene (HDPE). It may for example be a machined or moulded part.

The bone contact face 3 of the main body 2 of the implantable component 1 of the invention extends along a (unique) median contact plane Pc, advantageously, on the one hand, between an anterior edge 9 and an opposite posterior edge 10 along a anteroposterior AP direction of extension of the main body 2 and, on the other hand, between a lateral edge 11 and an opposite medial edge 12 along a lateromedial LM direction of extension of the main body 2. Preferably, said bone contact face 3 is substantially planar, as in the embodiment illustrated in the figures. Said bone contact face 3 is then advantageously intended to be arranged in direct contact with said area of the bone body Ti, Ta, area which will have been previously prepared to have a substantially planar corresponding surface. The main body 2 of the component 1 will then be advantageously intended to be positioned in direct plane-to-plane contact with said area of the bone body Ti, Ta. Even so, the bone contact face 3 could, as an alternative, not be strictly planar, although extending along said median contact plane Pc.

Preferably, the main body 2 of the implantable component 1 constitutes a monolithic part, formed of a material that is advantageously biocompatible and wear-resistant. Advantageously, said main body 2 is made of a metal material, for example titanium, chromium-cobalt alloy (CrCo), or also stainless steel. The main body 2 of the implantable component 1 is advantageously a casting part and/or a part machined from a block. Of course, other suitable materials can be contemplated, such as for example a ceramic material, a polymer material (PEEK, etc.) or also a composite material, as well as other manufacturing modes (injection, moulding, sintering, etc.), as long as the retained materials provide the main body 2 with a sufficient mechanical strength for the intended application.

In the preferential embodiment illustrated in the figures, in which the component 1 constitutes more specifically a tibial component 1, the main body 2 also comprises another face 13 (or lower face), opposite to said bone contact face 3, intended to come into contact with a separate intermediate component 7, as mentioned hereinabove. Advantageously, the lower face 13 of the main body 2 extends along a median plane that is substantially parallel to the median contact plane Pc, said tibial component 1 hence having generally the shape of a plate, of thickness typically comprised between 5 and 10 mm. As illustrated, the main body 2 of the tibial component 1 can also comprise a tibial medial face 14 and an opposite tibial lateral face 15, which connect the medial edge 12 and the lateral edge 11, respectively, of the bone contact face 3 to the lower face 13 of the main body 2. Advantageously, said medial body 12 of the main body 2 is substantially rectilinear and said tibial medial face 14 is substantially planar, so that the surgeon can position accurately said tibial component 1 into the patient's body, by aligning said tibial medial face 14 along a rectilinear cut made at the internal malleolus of the patient's ankle. This makes it possible to advantageously reduce the areas of bone cuts not covered, which could favour the appearance of *geodes* or cysts. Moreover, the main body 2 of the tibial component 1 can comprise a tibial anterior face 16 and an opposite tibial posterior face 17, which connect the anterior edge 9 and the posterior edge 10, respectively, of the bone contact face 3 to the lower face 13 of the main body 2.

It is to be noted that the terms "posterior", "anterior", "medial" and "lateral" are preferentially used in the present description to describe elements or features of the component 1 and the prosthesis 5 in relation with their respective orientation with respect to the patient's body, in normal use of said component 1 and prosthesis 5. Hence, the term "medial" is preferentially used for an element of the component 1 and/or the prosthesis 5 that is intended to be positioned on and directed to the side that is the closest to the medio-sagittal axis (or median axis) of the patient's body, in other words the side directed towards the inside of the patient's foot or leg. In contrast, the term "lateral" is used in relation with the side that is the farthest from the medio-sagittal axis. Following the same logic, the terms "posterior" and "anterior" preferably refer to a positioning backward and forward, respectively, with respect to the patient's front plane.

Still in the preferential embodiment illustrated in the figures, the tibial component 1 is designed to be fastened to said separate intermediate component 7, in order to advantageously suppress any degree of freedom between the tibial component 1 and the intermediate component 7. Such a fastening of these latter makes it possible to advantageously improve the stability of the prosthetic joint formed by the prosthesis 5. For that purpose, the tibial component 1 advantageously comprises a first fastening element 18 that is complementary to a second fastening element 19 carried by the intermediate component 7. For example, said first and second complementary fastening elements 18, 19 are designed in such a manner to allow a dovetail assembly of the intermediate component 7 to the tibial component 1. Hence, the lower face 13 of the tibial component 1 can advantageously be provided with a groove 18, for example of trapezoidal cross-section, which advantageously forms said first fastening element 18 (or female dovetail member). The intermediate component 7 can then be reciprocally provided with a tenon 19, forming said second fastening element 19 (or male dovetail member), of complementary shape and size with respect to those of said groove 18. Of course, a reverse configuration could perfectly be contemplated, said lower face 13 being provided with said tenon, said intermediate component 7 being reciprocally provided with said groove. Other suitable fastening means could also be contemplated.

As already mentioned hereinabove, the implantable component 1 of the invention comprises at least one anchoring means 4 that projects from the bone contact face 3 of the main body 2 of the component 1, to allow an anchoring of the latter into the concerned bone body Ti, Ta, i.e. into the bone mass of a distal end of a tibia Ti or a talus Ta. Said anchoring means 4 is advantageously intended to come, during the positioning of the implantable component 1 into the patient's body, into at least one corresponding accommodation formed previously and/or during the positioning of the implantable component 1 by the surgeon into the bone mass of the concerned bone body Ti, Ta. According to the invention, said anchoring means 4 comprises two pairs 20A, 20B of anchoring wings 21A, 22A, 21B, 22B, which each extend in a plane P1, P2, respectively, orthogonal to said median contact plane Pc of the bone contact face 3 between a first end 23A, 23B connected to said bone contact face 3 and an opposite (free) second end 24A, 24B, said respective planes of extension P1, P2 of the pairs 20A, 20B of anchoring wings 21A, 22A, 21B, 22B intersecting each other. The first and second planes of extension P1, P2 of the pairs 20A, 20B of anchoring wings 21A, 22A, 21B, 22B hence intersect each other along a line A-A' perpendicular to the median contact plane Pc of the bone contact face 3 of the main body 2 of the implantable component 1.

The anchoring means 4 of the implantable component 1 hence comprises:

- a first pair 20A of anchoring wings 21A, 22A, which are coplanar in a first plane of extension P1 orthogonal to said median contact plane Pc of the bone contact face 3, and a second pair 20B of anchoring wings 21B, 22B, which extend coplanar to each other in a second plane of extension P2, which is, on the one hand, orthogonal to said median contact plane Pc of the bone contact face 3 and which, on the other hand, intersects said first plan of extension P1 of the first pair 20A of anchoring wings 21A, 22A.

It is herein preferably meant by "wing", an element that mostly extends along a plane, with dimensions that are higher than a thickness measured in a direction perpendicular to said plane, and that is hence, as such, advantageously substantially flat, two-dimensional.

The orthogonality of the planes of extension P1, P2 of the pairs 20A, 20B of anchoring wings 21A, 22A, 21B, 22B advantageously simplify the preparation by the surgeon of the area of the bone body Ti, Ta in contact with which the main body 2 of the implantable component 1 is intended to be added to said bone body Ti, Ta. It also permits a particularly simple and accurate positioning and insertion, advantageously by impaction of the implantable component 1, of the anchoring means 4 into the bone mass of the bone body Ti, Ta, while favouring a close contact of the bone contact face 3 of the main body 2 of the implantable component 1 with said area of the bone body Ti, Ta. The intersecting nature of the planes of extension P1, P2 of the pairs 20A, 20B of anchoring wings 21A, 22A, 21B, 22B advantageously permit to fasten in a particularly reliable and efficient manner the implantable component 1 to the bone body Ti, Ta, by preventing in particular any translational or rotational movement of the main body 2 of the implantable component 1 with respect to said bone body TI, Ta.

In accordance with the invention, the second ends 24A, 24B of the pairs 20A, 20B of anchoring wings 21A, 22A, 21B, 22B are moreover inscribed in a leading plane Pa that is inclined with respect to the median contact plane Pc of the bone contact face 3 of the component 1, which significantly facilitate the insertion and the positioning of the implantable component 1 into the patient's body, between the distal end of the tibia Ti and the corresponding talus Ta of the patient's foot, while keeping a limited joint distraction.

The implementation of such an anchoring means 4 comprising two pairs 20A, 20B of anchoring wings 21A, 22A, 21B, 22B, which each extend in a plane P1, P2, respectively, orthogonal to the median contact plane Pc of the bone contact face 3 between a first end 23A, 23B connected to said bone contact face 3 and an opposite second end 24A, 24B (free), said respective planes of extension P1, P2 of the pairs 20A, 20B of anchoring wings 21A, 22A, 21B, 22B intersecting each other, said second ends 24A, 24B of the pairs 20A, 20B of anchoring wings 21A, 22A, 21B, 22B being inscribed in a leading plane Pa inclined with respect to said median contact plane Pc, is particularly advantageous in the particular case in which the implantable component 1 constitutes a tibial ankle-prosthesis component 1, insofar as notably the distal end of the tibia Ti is in practice far more difficult to access for the surgeon that the corresponding talus Ta, both for the preparation of the area intended to receive the tibial component 1 and for the later positioning and anchoring of the latter into the bone mass of the tibia Ti. Even so, the implementation of such an anchoring means 4 can also be interesting in the case in which the implantable component 1 of the invention constitutes a talar ankle-prosthesis component 6, insofar as the physical access to the talus Ta, which is far easier, nevertheless remains complex and limited in practice. Thus, the surgeon can perform more easily, more accurately and more rapidly, the operation of positioning the implantable component 1 of the invention, and more generally the prosthesis 5 comprising the latter.

The limitation of the joint distraction necessary for the positioning of the implantable component 1, and more generally of the ankle prosthesis 5, is moreover particularly beneficial for the patient, because it makes it possible to reduce the risk of tissue trauma associated with the operation of treatment of the patient's ankle, and hence to favour a rapid recovery of the latter.

According to a preferential variant, retained in the embodiment illustrated in the figures, the leading plane Pa is inclined with respect to the median contact plane Pc along a downslope from the anterior edge 9 to the posterior edge 10 of the bone contact face 3. Such a variant is particularly well-suited to an insertion and a positioning of the implantable component 1 into the patient's body by an anterior surgical approach (i.e. from the front of the patient's foot). As an alternative, the leading plane Pa could, conversely, be inclined with respect to the median contact plane Pc along a downslope from the posterior edge 10 to the anterior edge 9 of the bone contact face 3, for an insertion and a positioning of the implantable component 1 into the patient's body by a posterior surgical approach (i.e. from the rear of the patient's foot). As another alternative, the leading plane Pa could be inclined with respect to the median contact plane Pc along a downslope from the medial edge 12 to the lateral edge 11 of the bone contact face 3, for an insertion and a positioning of the implantable component 1 into the patient's body by a medial surgical approach (i.e. from the inner side of the patient's foot). However, considering the configuration of the human anatomical ankle, implantations by posterior or medial surgical approach generally prove to be of more complex and more risky implementation for the surgeon and for the patient, so that the anterior surgical approach is generally preferred.

Whatever the preferred surgical approach, and hence the slope direction of the retained leading plane Pa, the compromise between the reliability of the anchorage of the component 2 into the bone mass of the bone body Ti, Ta and the convenience of insertion and positioning of the implantable component 1 into the patient's body can be advantageously improved when the leading plane Pa is inclined with respect to the median contact plane Pc by an angle $\alpha$ comprised between 3° and 30°, preferably comprised between 3° and 15°, and also preferably comprised between 5° and 8°, and for example equal to about 6.3°.

Advantageously, the first ends 23A, 23B of the pairs 20A, 20B of anchoring wings 21A, 22A, 21B, 22B are directly connected in contact with the bone contact face 3, so that said pairs 20A, 20B of anchoring wings 21A, 22A, 21B, 22B extend from the latter to their respective second end 24A, 24B. Still more advantageously, said pairs 20A, 20B of wings 21A, 22A, 21B, 22B are directly connected in contact with the bone contact face 3, at their respective first ends 23A, 23B, by an edge. The junction between said pairs 20A, 20B of anchoring wings 21A, 22A, 21B, 22B and the surface of the bone contact face 3 of the main body 2 is hence advantageously devoid of fillet, or round transition area, which notably allows facilitating an accurate and close contact of the bone contact face 3 with the corresponding area of the bone body Ti, Ta during the positioning of the component 1 into the patient's body. As an alternative, the bone contact face 3 could be provided with a cup from the bottom of which the pairs 20A, 20B of anchoring wings 21A, 22A, 21B, 22B would extend with a fillet whose height would be lower than the depth of the cup, so that the fillet would not extend beyond the surface of the bone contact face 3.

Advantageously, as in the preferential embodiment illustrated in the figures, the wings 21A, 22A, 21B, 22B of each pair 20A, 20B of anchoring wings 21A, 22A, 21B, 22B extend each other from the intersection line A-A' of the respective planes of extension P1, P2 of said pairs 20A, 20B of anchoring wings 21A, 22A, 21B, 22B. Each pair 20A, 20B of anchoring wings 21A, 22A, 21B, 22B thus extends in a substantially continuous way, which notably allows simplifying the design and the manufacturing of the anchoring means 4 and the implantable component 1.

In order, in particular, to simplify the design of the component 1 and to balance at best the anchoring of the component 1 according to the respective directions of the planes of extension P1, P2 of the two pairs 20A, 20B of wings 21A, 22A, 21B, 22B, the wings 21A, 22A, 21B, 22B of each of said pairs 20A, 20B of anchoring wings 21A, 22A, 21B, 22B are preferentially shaped in such a manner that their orthogonal projections on the median contact plane Pc are symmetrical to each other with respect to the plane of extension P1, P2 of the other of said pairs 20A, 20B of anchoring wings 21A, 22A, 21B, 22B. Thus, as Illustrated in the figures, the wings 21A, 22A of the first pair 20A of wings 21A, 22A are shaped so that their respective orthogonal projections on the median contact plane Pc are advantageously symmetrical to each other with respect to the plane of extension P2 of the second pair 20B of wings 21B, 22B, and, reciprocally, the wings 21B, 22B of the second pair 20B of wings 21B, 22B are shaped so that their respective orthogonal projections on the median contact plane Pc are advantageously symmetrical to each other with respect to the plane of extension P1 of the first pair 20A of wings 21A, 22A.

As illustrated in the figures, each of said anchoring wings 21A, 22A, 21B, 22B is advantageously provided with a lateral external edge 25A, 26A, 25B, 26B that connects to each other the first and second edges 23A, 23B, 24A, 24B of pairs 20A, 20B of anchoring wings 21A, 22A, 21B, 22B. Said lateral external edges 25A, 26A, 25B, 26B of the wings 21A, 22A, 21B, 22B of a same pair 20A, 20B of wings 21A, 22A, 21B, 22B extend preferentially along median directions B-B', C-C', D-D', E-E' that are oblique and convergent as they go away from the median contact plane Pc. The lateral external edges 25A, 26A, 25B, 26B hence extend in an inclined, oblique, manner with respect to the median contact plane Pc, along median directions B-B', C-C', D-D', E-E' that, moreover, intersect two-by-two at intersection points located beyond the median contact plane Pc and the leading plane Pa, so that the lateral external edges 25A, 26A, 25B, 26B of the wings 21A, 22A, 21B, 22B of a same pair 20A, 20B of wings 21A, 22A, 21B, 22B are hence not parallel to each other. The lateral external edges 25A, 26A of the wings 21A, 22A of the first pair 20A of anchoring wings 21A, 22A hence advantageously extend along median directions B-B', C-C', respectively, forming between each other a first angle $\beta 1$, whereas the lateral external edges 25B, 26B of the wings 21B, 22B of the second pair 20B of anchoring wings 21B, 22B hence advantageously extend along median directions D-D', E-E', respectively, forming between each other a second angle $\beta 2$. To simplify the design of the anchoring means 4, said first and second angles $\beta 1$, $\beta 2$ are preferentially chosen with identical values. Such a configuration of the lateral external edges 25A, 26A, 25B, 26B of the wings 21A, 22A, 21B, 22B advantageously contributes to an easy insertion, in particular by impaction, of the anchoring means 4 into the bone mass of the considered bone body Ti, Ta.

Still more preferentially, the wings 21A, 22A, 21B, 22B of each of said pairs 20A, 20B of wings 21A, 22A, 21B, 22B are shaped so that their orthogonal projections on the median contact plane Pc are symmetrical between each other with respect to the plane of extension P1, P2 of the other of said pairs 20A, 20B of wings 21A, 22A, 21B, 22B, and the lateral external edges 25A, 26A, 25B, 26B of the wings 21A, 22A, 21B, 22B of a same pair 20A, 20B of wings 21A, 22A, 21B, 22B extend along oblique and convergent median directions B-B', C-C', D-D', E-E', as contemplated hereinabove. Hence, the lateral external edges 25A, 26A, 25B, 26B of the wings 21A, 22A, 21B, 22B of each of the pairs 20A, 20B of wings 21A, 22A, 21B, 22B are inscribed in a fictive cone of revolution that extends in height along a line merged with the intersection line A-A' of the planes of extension P1, P2 of the pairs 20A, 20B of wings 21A, 22A, 21B, 22B. Thus, the anchoring means 4 can be positioned into the bone mass, in particular by impaction, in a particularly easy and accurate manner, along a well-controlled implantation trajectory. Besides, such a shape of the anchoring means 4 is particularly well adapted in the particular case in which the implantable component 1 constitutes a tibial component 1, considering the wholly conical shape of the distal end of the tibia Ti (FIG. 8).

Advantageously, said median directions of extension B-B', C-C', D-D', E-E' of the lateral external edges 25A, 26A, 25B, 26B of the wings 21A, 22A, 21B, 22B of a same pair 20A, 20B of wings 21A, 22A, 21B, 22B intersect each other by an angle $\beta 1$, $\beta 2$ comprised between 3° and 75°, and preferably comprised between 10° and 30°. Still more preferentially, said angle $\beta 1$, $\beta 2$ is substantially equal to 20°, so as notably to permit the implementation of large widths of wings 21A, 22A, 21B, 22B, and hence to optimize the anchorage strength, while limiting the risk of interaction of said wings 21A, 22A, 21B, 22B with the cortical bone of the tibia Ti, harder than the bone material forming the central portion of the tibia Ti and hence liable to oppose to the perfect insertion of the anchoring means 4, in the case in which the implantable component 1 constitutes a tibial component 1. Such an angle $\beta 1$, $\beta 2$ value can also be interesting regarding the mechanical strength of the anchoring means 4 in the bone mass, in the case where the implantable component 1 constitutes a talar component for an ankle prosthesis, although the absence of cortical portion at the talus Ta can potentially allow an angle $\beta 1$, $\beta 2$ value higher than 20°.

Advantageously, the wings 21A, 22A, 21B, 22B of the anchoring means 4 of the implantable component 1 extend between their first and second ends 23A, 23B, 24A, 24B over a height Hmin, Hmax at least equal to 3 mm and at most equal to 30 mm, in particular in the case in which the implantable component 1 constitutes a tibial component 1 (as in the preferential embodiment illustrated in the figures). As illustrated in FIGS. 2 to 4, said height of the wings 21A, 22A, 21B, 22B is advantageously measured from the surface of the bone contact face 3 of the main body 2, perpendicular to the median contact plane Pc along which said bone contact face 3 extends. Considering the inclination, with respect to the median contact plane Pc, of the leading plane Pa in which the respective second ends 24A, 24B of the pairs 20A, 20B of anchoring wings 21A, 22A, 21B, 22B are inscribed (and independently of the value of the inclination angle $\alpha$ of said leading plane Pa), the point(s) of said second ends 24A, 24B the closest to the surface of the bone contact face 3 is hence positioned at a distance Hmin of at least 3 mm from the latter. Reciprocally, the point(s) of said second ends 24A, 24B the farthest from the surface of the bone contact face 3 is hence positioned at a distance Hmax of at most 30 mm from the latter. A so-optimized height of the wings 21A, 22A, 21B, 22B of the anchoring means 4 advantageously contributes to obtaining an excellent compromise between, on the one hand, the robustness and reliability of anchorage of the main body 2 of the implantable component 1 into the bone mass of the bone body Ti, Ta and the limitation of the risk of damaging the latter by the anchoring means 4, and, on the other hand, the facility of positioning said component 1 into the patient's body (both as regards the previous preparation of the bone area and as regards the implantation of the implantable component 1 itself).

In practice, said height Hmin, Hmax can be chosen according to the context of implantation. For example, in the case of a first implantation operation for a given ankle, the minimum height Hmin can be advantageously chosen at least equal to 3 mm, and the maximum height Hmax can be advantageously chosen at most equal to 15 mm. For a revision operation, that is to say aiming to replace an existing implant at a given ankle, the minimum height Hmin can advantageously be chosen at least equal to 15 mm, and the maximum height Hmax can advantageously be chosen at most equal to 30 mm.

The wings 21A, 22A, 21B, 22B of the anchoring means 4 each have preferably a mean thickness e1, e2 comprised between 1 mm and 3 mm, preferably equal to about 1.5 mm. Such a thickness e1, e2 allows notably providing the wings 21A, 22A, 21B, 22B with a sufficient rigidity, on the one hand to avoid a torsion of the wings 21A, 22A, 21B, 22B during the positioning of the implantable component 1, in particular when the latter is made by impaction, and on the other hand, to guarantee an excellent anchoring of the implantable component 1 into the bone mass and a high intrinsic robustness of the anchoring means 4. Moreover, the fact that the wings 21A, 22A, 21B, 22B remain nevertheless relatively thin makes it possible to limit the volume of bone mass to be removed during the preparation of the concerned bone area and/or to be replaced by the anchoring means 4, which simplifies the operation of preparation of the bone body Ti, Ta and favours the strength of the anchoring means 4, while respecting at best the anatomical integrity.

Preferably, the anchoring means 4 is arranged substantially at the centre of the bone contact face 3 of the main body 2 of the implantable component 1. Once implanted in the bone mass of the concerned bone body Ti, Ta, the component 1 will hence have a further improved mechanical strength, the risk of rotation of the component 1 in a direction orthogonal to the median contact plane Pc of the bone contact face 3 of its main body 2 being that way limited. In the case in which said implantable component 1 constitutes a tibial component 1 for an ankle prosthesis 5, it is hence advantageously possible for the surgeon, during the positioning of the component 1 into the patient's body, to align the intersection line A-A' of the planes of extension P1, P2 of the pairs 20A, 20B of wings 21A, 22A, 21B, 22B with the respective mean axis of extension of the patient's tibia Ti, so as to ensure a good distribution of the compression forces exerted on the implantable component 1.

Advantageously, the anchoring means 4 forms, as such, a monolithic part, that is to say that the two pairs 20A, 20B of wings 21A, 22A, 21B, 22B are integral with each other, which allows simplifying the design and the manufacturing of the anchoring means 4. As an alternative, each of the wings 21A, 22A, 21B, 22B or each of the pairs 20A, 20B of wings 21A, 22A, 21B, 22B could be separate from each other and be assembled to these latter by welding or by fitting, for example. Still more advantageously, the anchoring means 4 forms a monolithic part with the main body 2 of the implantable component 1. There is hence continuity of material between the main body 2 and the anchoring means 4, and these latter can then be manufactured simultaneously, in a simple, rapid and cost-effective way. Advantageously, the main body 2 and the anchoring means 4 can then be both made of a metal material, for example titanium, chromium-cobalt alloy (CrCo), or also stainless steel. It remains conceivable that the anchoring means 4, monolithic or not, can be separate from the main body 2, and be designed to be fastened to the latter (for example by screwing or snap-in), before or during the positioning of the implantable component 1 into the patient's body. Even so, such a design is less advantageous, both in terms of reliability and robustness of the link between the main body 2 and the anchoring means 4, and in terms of convenience of implementation of the implantable component 1 for the surgeon. Moreover, the use of an assembly of a plurality of separate parts tends to increase the complexity, and hence the cost, of design and manufacturing. Whether or not the anchoring means 4 forms, as such, a monolithic part, it is advantageous to provide that the pairs 20A, 20B of anchoring wings 21A, 22A, 21B, 22B of said anchoring means 4 are connected to each other at the intersection of their respective planes of extension P1, P2 by fillets 27A, 28A, 27B, 28B, and not by a simple rectilinear edge (FIG. 5). Such fillets 27A, 28A, 27B, 28B can then have a radius of curvature preferentially comprised between 2 mm and 15 mm. The intrinsic mechanical strength of the anchoring means 4 is hence reinforced, and the risk of formation of empty spaces near the intersection of the pairs 20A, 20B of wings 21A, 22A, 21B, 22B, once the anchoring means 4 introduced into the bone mass of the considered bone body Ti, Ta, is moreover limited.

According to a preferential variant, retained in the embodiment illustrated in the figures, the planes of extension P1, P2 of the first and second pairs 20A, 20B of wings 21A, 22A, 21B, 22B are perpendicular to each other. The anchoring means 4 has hence advantageously a shape of "+", viewed in cross-section in a plane parallel to the median contact plane Pc. Such a design of the pairs 20A, 20B of wings 21A, 22A, 21B, 22B is particularly simple to implement and allows an excellent anchoring of the anchoring means 4 in the bone mass. Moreover, when said pairs 20A, 20B of wings 21A, 22A, 21B, 22B are directly connected to the bone contact face 3 by their first ends 23A, 23B, such a design also advantageously makes it possible to provide the pairs 20A, 20B of wings 21A, 22A, 21B, 22B with a function of mechanical rigidification of the main body 2. Such an additional function can be particularly interesting when the main body 2 has the shape of a plate, as contemplated hereinabove and illustrated by way of example in the figures, which could be subject to a risk of torsion, bending (in particular, mediolateral bending), under the effect of the mechanical forces exerted on the implantable component 1 and the prosthesis 5 during the use. Preferably, said pairs 20A, 20B of wings 21A, 22A, 21B, 22B are respectively arranged substantially parallel to said mean anteroposterior AP and lateromedial LM direction of extension of the main body 2 of the implantable component 1, so as to define respectively a pair 20A of anteroposterior wings 21A, 22A and a pair 20B of lateromedial wings 21B, 22B. This permits in particular to further simplify the design and the manufacturing of the implantable component 1, and, in a certain extend, to further facilitate the positioning into the patient's body by the surgeon, wherein said pair 20A of anteroposterior wings 21A, 22B can play the role of a visual reference.

Still more preferentially, said pair 20A of anteroposterior wings 21A, 22A has, at its first end 23A, and along said mean anteroposterior AP direction of extension, a width L1 that is larger than a width L2 that said pair 20B of lateromedial wings 21B, 22B takes at its respective first end 23B and along said mean lateromedial LM direction of extension (FIGS. 2 to 5). Advantageously, the pair 20A of anteroposterior wings 21A, 22A has hence, at its first end 23A and along said mean anteroposterior AP direction of extension, a width L1 comprised between 10 mm and 30 mm, and preferably equal to about 18 mm. Reciprocally, the pair 20B of lateromedial wings 21B, 22B has, at its first end 23B and along said mean lateromedial LM direction of extension, a width L2 comprised between 10 mm and 30 mm, and preferably equal to about 16 mm. This advantageously allows optimizing the anchoring of the implantable component 1 into the bone mass, while limiting the risk of fragilization of the latter, insofar a both the distal end of an anatomical tibia Ti and an anatomical talus Ta have generally an anteroposterior size greater than the mediolateral size. Even so, according to a not-illustrated and less advantageous alternative variant, the planes of extension P1, P2 of the first and second pairs 20A, 20B of wings 21A, 22A, 21B, 22B could be non-perpendicular to each other. The planes of extension P1, P2 would then define between each other a pair of obtuse angles and a pair of acute angles, and the anchoring means 4 would then have an "X"-shape.

Advantageously, the second free ends 24A, 24B of the pairs 20A, 20B of anchoring wings 21A, 22A, 21B, 22B delimit bevelled leading edges, as illustrated by way of example in the figures, so as to facilitate the penetration and the insertion of the anchoring means 4 into the bone mass, in particular by impaction, while limiting the risk of damage of said bone mass. Advantageously, the lateral external edges 25A, 26A, 25B, 26B of each of said pairs 20A, 20B of anchoring wings 21A, 22A, 21B, 22B are substantially flat, that is to say they extend respectively in a plane orthogonal to the plane of extension P1, P2 of said pair 20A, 20B of wings 21A, 22A, 21B, 22B. This also helps in simplifying the design and the manufacturing of the anchoring means 4 and of the implantable component 1. Moreover, such flat lateral external edges 25A, 26A, 25B, 26B advantageously allow limiting, in a certain extent, the risk of translation of the implantable component 1 along a direction of the planes of extension P1, P2 during the insertion of the anchoring means 1 into the bone mass, and later during the use of the implantable component 1 and the prosthesis 5. As an alternative, said lateral external edges 25A, 26A, 25B, 26B could be chamfered, or also bevelled, to facilitate the insertion of the anchoring means 4 into the bone mass during the positioning of the implantable component 1 into the patient's body.

Advantageously, said implantable component 1 is devoid of any means, other than said anchoring means 4, provided to anchor the main body 2 of the implantable component 1 into the bone mass of the bone body Ti, Ta. In particular, the implantable component 1 advantageously comprises neither a pad nor an anchoring pin complementary to said anchoring means 4 comprising said pairs 20A, 20B of anchoring wings 21A, 22A, 21B, 22B. Said anchoring means 4 hence substantially ensures alone the fastening of the main body 2 of the component 1 into the bone mass of the bone body Ti, Ta. The design and the manufacturing of the implantable component 1, and hence of the ankle prosthesis 5 to which it belongs, are hence simplified. Moreover, the positioning of the implantable component 1 into the patient's body is then more simple, more rapid, less painful and less traumatic for the patient, notably due to the simplification of the preparation of the bone area intended to receive the component 1, because it is, in particular, not necessary to provide a plurality of pre-holes in the bone mass for receiving a plurality of separate anchoring means. However, it remains of course possible to provide on the contrary that the implantable component 1 comprises, in addition to said anchoring means 4 comprising said pairs 20A, 20B of wings 21A, 22A, 21B, 22B, separate complementary anchoring means, as for example one or several pad(s) or pin(s), themselves protruding from the bone contact face 3 of the main body 2 of the implantable component 1, then preferably along a direction of extension orthogonal to the median contact plane Pc of the bone contact face 3.

Optionally, the wings 21A, 22A, 21B, 22B of the anchoring means 4 can be openwork, i.e. provided with one or several through-orifices or apertures, so as to further favour the anchoring of the implantable component 1 into the bone mass by growth of the bone inside the orifices or apertures and the formation of bone bridges on either side of the wings 21A, 22A, 21B, 22B. It will then nevertheless be very tricky to later extract said component 1 from the patient's body without risk of degradation of the bone mass surrounding the anchoring means 4 thereof. Preferably, as illustrated as an example in the figures, the wings 21A, 22A, 21B, 22B of the anchoring means 4 are on the contrary solid, i.e. non-openwork, which hence permits facilitating a potential future extraction of the implantable component 1 from the patient's body, for example in order to replace said component 1 by another implantable component in case of wearing, deterioration with use.

Optionally, all or part of the bone contact face 3 of the main body 2 of the implantable component 1 and/or of the surface of the wings 21A, 22A, 21B, 22B of the anchoring means 4 of the implantable component 1 can be provided with a particular surface coating (for example, made of porous titanium or hydroxyapatite), in order to favour the bone adhesion of the main body 2 and/or of the anchoring means 4 of the implantable component 1 to the bone body Ti, Ta to which said component 1 is intended to be fastened.

In the embodiment of the ankle prosthesis 5 illustrated in FIG. 7, only the tibial component 1 is an implantable component 1 in accordance with the invention. In this embodiment, the talar component 6 of the prosthesis 5 comprises a talar main body 29 provided with a talar bone contact face 30 intended to be arranged in contact with an area of the talus Ta of an ankle and opposite to the talar joint surface 8 mentioned hereinabove.

Said talar bone contact face 30 extends in a (unique) median contact plane. The talar component 6 further comprises a talar anchoring means 31 formed of a pair of anchoring pads 31, of circular cross-section cylindrical shape, to ensure an anchoring of the talar component 6 into the bone mass of the talus Ta. Advantageously, each of said anchoring pads 31 extends longitudinally from the talar bone contact face 3 along an oblique direction with respect to the latter.

According to alternative embodiments (not illustrated), it is possible that the talar bone contact face 30 does not extend in a unique median contact plane but, for example, in two intersecting median contact planes. As an alternative, the talar anchoring means 31 could be formed of a unique anchoring pad, for example of circular cross-section cylindrical shape, or also be formed of an anchoring pin of cylindrical or frustoconical shape. Advantageously, such a unique anchoring pad or such an anchoring pin would then extend longitudinally from the talar bone contact face along an oblique direction with respect to the latter.

The implementation of the implantable component 1 and the prosthesis 5 of the invention, in their embodiment illustrated in the figures, can, for example and basically, be carried out as follows:

An incision is made into the skin and the soft tissues of the patient's ankle to be treated, preferably at the front face of the ankle so as to provide access to the tibiotalar joint by an anterior surgical approach;

A planar bone cut is made horizontally (with respect to the natural vertical position of the patient in upright posture), at the distal end of the tibia Ti, preferably using a suitable cutting guide, so as to form a substantially planar bone area intended to come into contact with the bone contact face 3 of the tibial component 1;

One or several bone cuts are made into the talus Ta, so as to form a bone area that is planar or provided with a plurality of intersecting planar portions, and intended to come into contact with the talar bone contact face 30 of the talar component 6;

One or several talar pre-holes, intended to receive the talar anchoring means 31 of the talar component 6, are made into said prepared bone area of the talus Ta;

A tibial pre-hole intended to receive the anchoring means 4 of the tibial component 1 is made into said prepared bone area of the tibia Ti, using a tibial drilling guide provided with a through-orifice whose perimeter has a shape that is complementary of the cross-section of the anchoring means 4 and an impaction pre-drilling means provided with a working portion of shape substantially identical to that of said anchoring means 4. After having temporary fastened the tibial drilling guide in contact with the planar bone area of the tibia Ti, the tibial pre-hole is made by slidingly introducing the working portion of the pre-drilling means into the corresponding through-orifice of the tibial drilling guide, then by forcibly inserting by impaction said working portion into the bone mass of the tibia Ti;

After removal of the tibial drilling guide, the tibial component 1 is positioned and held in the patient's body, the bone contact face 3 of the main body 2 of the tibial component 1 coming opposite the planar bone area previously prepared at the distal end of the tibia Ti, then the anchoring means 4 of the tibial component 1 is forcibly inserted by impaction into the tibial pre-hole;

The talar component 6 is positioned and held in the patient's body, the talar bone contact face 30 of the talar component 6 coming opposite the bone area previously prepared at the talus Ta, then the anchoring means 31 of the talar component is forcibly inserted by impaction into the talar pre-hole(s);

The intermediate component 7 of the prosthesis 5 is inserted into the patient's body, so as to interpose between the tibial component 1 and the talar component 6, the tenon 19 of the intermediate component 7 sliding in the corresponding groove 18 of the tibial component 1, so as to fasten the intermediate component 7 to the tibial component 1;

The patient's body is closed by any suitable means and according to any suitable technique.

The invention claimed is:

1. An implantable ankle-prosthesis device, comprising:

a tibial component comprising a main body provided with a bone contact face configured to come in contact with an area of a bone body of an ankle that extends along a median contact plane;

at least one projection that protrudes from the bone contact face to anchor the tibial component into the bone body;

the projection comprising two pairs of anchoring wings which each extend in a plane, respectively, orthogonal to the median contact plane of the bone contact face between a first end connected to the bone contact face and an opposite second end;

wherein the pairs of anchoring wings comprise a first width in an anteroposterior direction of extension that is larger than a second width in a lateromedial extension;

the respective planes of extension of the pairs of anchoring wings intersecting each other;

wherein the bone contact face of the tibial component is configured to come in contact with an area of a distal end of a tibia;

wherein the intersecting planes of extension of the anchoring wings are configured to permit insertion of the tibial component by impaction while preventing translational or rotational movement of the main body relative to the tibia;

the tibial component comprising a first fastening element that is complementary to a second fastening element carried by an intermediate component;

wherein the second ends of the pairs of anchoring wings are inscribed in a leading plane that is inclined with respect to the median contact plane along a downslope from an anterior edge to posterior edge of the bone contact face; and wherein the wings of each of said pairs of wings of the projection are provided with lateral external edges that extend in an inclined, oblique, manner with respect to the median contact plane, along one or more median directions that intersect at intersection points located beyond the median contact plane and the leading plane, such that the lateral external edges of the wings of a same pair of wings are not parallel.

2. The implantable ankle-prosthesis device according to claim 1, wherein the leading plane is inclined with respect to the median contact plane by an angle ($\alpha$) ranging between 3° and 30°.

3. The implantable ankle-prosthesis device according to claim 1, wherein the bone contact face extends between the anterior edge and the opposite posterior edge, and between a lateral edge and an opposite medial edge.

4. The implantable ankle-prosthesis device of claim 1, wherein the wings of each of said pairs of anchoring wings are shaped so that their orthogonal projections on the median contact plane are symmetrical to each other with respect to the plane of extension.

5. The implantable ankle-prosthesis device of claim 1, wherein the lateral external edges of the wings extend along median directions (B-B', C-C', D-D', E-E') that are oblique and convergent as they go away from the median contact plane.

6. The implantable ankle-prosthesis device of claim 5, wherein median directions of extensions of lateral external edges of the wings of a same pair of wings intersect each other by an angle ($\beta 1$, $\beta 2$) ranging between 3° and 75°.

7. The implantable ankle-prosthesis device of claim 1, wherein the wings of the projection extend between said first and second ends over a height comprising a range between 3 mm and 30 mm.

8. The implantable ankle-prosthesis component of claim 1, wherein the wings of the projection each have a mean thickness comprised between 1 mm and 3 mm.

9. The implantable ankle-prosthesis device of claim 1, wherein the planes of extension of the pairs of wings are perpendicular to each other and arranged substantially parallel to mean anteroposterior and lateromedial directions of extension of the main body of the tibial component, thereby defining a pair of anteroposterior wings a pair of lateromedial wings.

10. The implantable ankle-prosthesis device of claim 1, wherein the projection is arranged substantially at the center of the bone contact face of the main body of the tibial component.

11. The implantable ankle-prosthesis device of claim 1, wherein the projection forms a monolithic part.

12. The implantable ankle-prosthesis device of claim 1, wherein the projection forms a monolithic part with the main body of the tibial component.

13. The implantable ankle-prosthesis device of claim 1, wherein the pairs of wings are connected to each other at the intersection of their respective planes of extension by a plurality of fillet having a radius of curvature ranging between 2 mm and 15 mm.

* * * * *